(12) United States Patent
Zahynacz et al.

(10) Patent No.: US 10,918,552 B2
(45) Date of Patent: Feb. 16, 2021

(54) LIMB POSITIONING APPARATUS AND METHODS OF USE THEREOF

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Daniel Zahynacz, Somerville, MA (US); William D. Obendorf, Chelmsford, MA (US)

(73) Assignees: Smith & Nephew, Inc., Memphis, TN (US); Smith & Nephew Orthopaedics AG; Smith & Nephew Asia Pacific Pte. Limited, Singapore (SG)

( * ) Notice: Subject to any disclaimer, the term of this patent is extended or adjusted under 35 U.S.C. 154(b) by 169 days.

(21) Appl. No.: 16/417,850

(22) Filed: May 21, 2019

(65) Prior Publication Data
US 2020/0368089 A1   Nov. 26, 2020

(51) Int. Cl.
*A61G 13/12* (2006.01)
*A61F 5/37* (2006.01)

(52) U.S. Cl.
CPC ........ *A61G 13/1235* (2013.01); *A61F 5/3761* (2013.01)

(58) Field of Classification Search
CPC ............ A61G 13/1245; A61G 13/1235; A61G 13/122; A61G 13/123; A61G 13/101; A61G 13/129; A61G 13/04; A61G 13/08; A61G 13/1225; A61G 13/124; A61G 13/1295; A61G 7/10; A61G 13/0009; A61G 15/12; A61G 7/0755; A61G 7/075; A61G 13/1255; A61G 2200/32; A61G 5/122; A61G 5/127; A61G 7/0002; A61G 7/015; A61G 7/08; A61G 7/1013; A61G 13/0072; A61G 13/06; A61G 13/12; A61G 13/00; A61G 13/126; A61G 13/0036; A61G 13/0045; A61F 5/3761; A61F 5/048; A61F 5/04; A61H 1/02; A61H 1/0218; A61H 1/0229; A61B 19/12; A61B 19/00; A61B 46/27
See application file for complete search history.

(56) References Cited

U.S. PATENT DOCUMENTS 4,930,523 A * 6/1990 Laico ................. A61F 5/04
5/87.1

* cited by examiner

*Primary Examiner* — Ophelia A Hawthorne
(74) *Attorney, Agent, or Firm* — Burns & Levinson, LLP; Joseph M. Maraia; Mario Schepper Grolnic

(57) ABSTRACT

A limb positioning apparatus comprises a vertical post connected to the operating table near the shoulder of the patient and a boom member connected to the vertical post through a hinge. The hinge allows the angle between the vertical post and the boom member to be adjusted with assistance from a lockable gas spring attached to the hinge. The vertical post and the boom member house the internal cables for transferring the primary traction load to the operative limb.

20 Claims, 4 Drawing Sheets

LIMB POSITIONING APPARATUS AND METHODS OF USE THEREOF

FIELD

This disclosure relates generally to limb positioning devices and, more particularly, to devices which are used to position the shoulder and arm of a patient during shoulder surgery.

BACKGROUND

Orthopedic shoulder surgery involves complexities not encountered in other surgeries, such as knee surgery. For example, during shoulder surgery, ports or incisions are placed through a patient's shoulder joint to provide access for instruments such as light sources, visual scopes, and surgical tools. However, it is sometimes desirable for a surgeon to gain access to a different area of the joint, without creating new ports, by rotating the operative limb and holding it in a new position. This is usually done manually by a physician's assistant who must rotate and hold the arm in a new fixed position for as long as needed to allow the surgeon to complete the required tasks. This prevents the assistant from doing anything else during this time, and can result in fatigue for the assistant, leading to inconsistent positioning of the patient's arm.

Specialized mechanical positioning devices have been developed for supporting and positioning a patient's shoulder joint during surgery. However, such limb positioning devices are commonly mounted to the foot of the operating table and oriented towards the operative limb of the patient. Thus, when mounted to the foot of the table, the center of rotation for the shoulder and for the system hinge are at two different geometric locations. This can limit the obtainable abduction angle of the shoulder.

BRIEF SUMMARY

Described herein is a limb positioning apparatus comprised of a vertical post connected to the operating table near the shoulder of the patient and a boom member connected to the vertical post through a hinge. The hinge allows the angle between the vertical post and the boom member to be adjusted with assistance from a lockable gas spring attached to the hinge. The vertical post and the boom member house the internal cables for transferring the primary traction load to the operative limb. The apparatus is advantageously designed to place the centers of rotation of the shoulder and the hinge closer together, allowing the apparatus to replicate and follow the natural range of motion of the shoulder joint. This allows greater intraoperative control of arm positioning.

Further examples of the limb positioning apparatus of this disclosure may include one or more of the following, in any suitable combination.

Examples of the limb positioning apparatus of this disclosure include a support member having a proximal end and a distal end. The proximal end is configured to be attached to a table adjacent a shoulder of an arm of a patient. A boom member extends above and is moveable relative to the support member via a hinge assembly coupled between the distal end of the support member and a proximal end of the boom member. The boom member is configured to extend along the arm of the patient. A cable/traction system extends through the support member and the boom member. A distal end of the cable system is configured to be attached to the arm of the patient and a proximal end of the cable system is configured to be attached to a weight for providing traction to the arm of the patient. A gas spring is operatively connected between the support member and the boom member. The gas spring is configured to assist with the movement of the boom member relative to the support member.

In further examples, the cable/traction system includes a carriage disposed within the boom member and moveable along the boom member. A first flexible member is attached to a first side of the carriage. A free end of the first flexible member is configured for attachment to the weight. A second flexible member is attached to a second side of the carriage. The second flexible member is configured for attachment to the arm of the patient. In examples, the first flexible member is attached to the first side of the carriage such that first flexible member can rotate relative to a longitudinal axis of the boom member. In examples, the second flexible member is attached to the second side of the carriage such that second flexible member cannot rotate relative to a longitudinal axis of the boom member. In examples, the second flexible member is routed through a plurality of pulleys such that the plurality of pulleys provide an anti-rotational resistance to the second flexible member. In examples, a diameter of the second flexible member is selected to be larger than a diameter of the first flexible member. In examples, the carriage is a wheeled carriage. In examples, the proximal end of the support member is configured to be attached to the table by a clamp such that the first flexible member extends through the clamp. In examples, the support member is rotatable relative to the clamp. In examples, at least one of the support member and the boom member is a square tube. In examples, the gas spring includes a lever for locking and unlocking the gas spring. Examples of the apparatus further include a lift bar extending from the support member for supporting an underside of the arm of the patient. In examples, a distal end of the lift bar includes a padded member.

Examples of a method of positioning a limb during surgery of this disclosure include attaching an arm of a patient to a limb positioning apparatus. The limb positioning apparatus includes a support member having a proximal end and a distal end. The proximal end is configured to be attached to a table adjacent a shoulder of the arm of the patient. A boom member extends above and is moveable relative to the support member via a hinge assembly coupled between the distal end of the support member and a proximal end of the boom member. The boom member is configured to extend along the arm of the patient. A cable/traction system extends through the support member and the boom member. A distal end of the cable system is configured to be attached to the arm of the patient and a proximal end of the cable system is configured to be attached to a weight for providing traction to the arm of the patient. A gas spring is operatively connected between the support member and the boom member. The boom member is moved relative to the support member such that the operative limb of the patient is placed in a pre-selected position.

Further examples of the method include actuating a lever of the gas spring such that the boom member is moveable relative to the support member. Further examples include locking the boom member relative to the support member by actuating a lever of the gas spring. Further examples include attaching the limb positioning apparatus to the table adjacent the shoulder of the patient with a clamp such that the proximal end of the cable system extends through the clamp. Further examples include rotating the support member relative to the clamp. In examples, the cable/traction system is self-adjusting in length as the boom member is moved relative to the support member. Examples of the method further include supporting the arm of the patient with a lift bar extending from the support member toward the patient.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1:
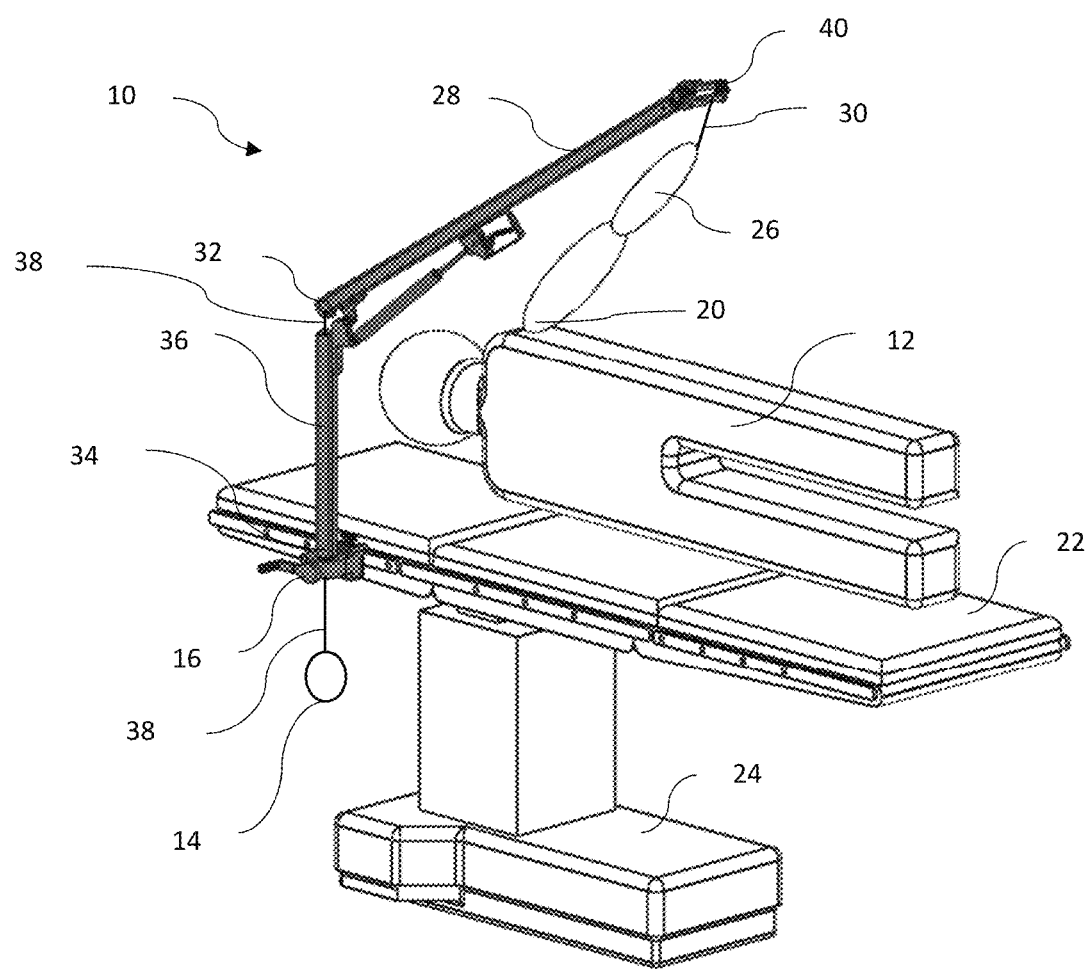
FIG. 1 is an example of a limb positioning apparatus of this disclosure attached to an operating table near a shoulder of a patient.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "up," "down," "above," "below" and the like is intended only to help in the clear description of the present disclosure and are not intended to limit the structure, positioning and/or operation of the disclosure in any manner.

Referring now to FIG. 1, an example of a limb positioning apparatus 10 of this disclosure is illustrated, the component parts of which are described in more detail below. In FIG. 1, a patient 12 is shown lying on a standard operating table 22 and prepared for a surgical operation. The operating table 22 is supported by a suitable stand or support 24 on the floor of the operating room. At least a portion of the operable arm 26 of the patient 12 is attached to and covered by a sterile drape assembly (not shown). A non-limiting example of the drape assembly is described in International Publication No. WO 2018/140346 to Smith Nephew, Inc. (Memphis, Tenn.), the entire contents of which are incorporated herein by reference. A proximal end 32 of a boom member 28 is hingedly attached to a support member, such as a vertical post 36, as further described below. The vertical post 36 is fixedly secured to the operating table 22 by a rail clamp 16 at a position adjacent the shoulder 20 of the patient 12. The rail clamp 16 may be configured such that the vertical post 36 is rotatable relative to the rail clamp 16 for positioning the arm 26. A non-limiting example of a rail clamp 16 is described in International Publication No. WO 2019/023334 to Smith E Nephew, Inc. (Memphis, Tenn.), the entire contents of which are incorporated herein by reference.

Still referring to FIG. 1, a cable/traction system of the apparatus 10 includes a flexible drive shaft 30, which may be a metal cord, secured to the drape assembly and routed internally through the boom member 28. The drive shaft 30 may include a rotational control (not shown) between the drive shaft 30 and the drape assembly, so that the drape assembly is rotatable relative to the drive shaft 30 for positioning the arm 26. A load bearing cable 38, which may be a wire rope, is connected to the drive shalt 30 within the boom member 28 and extends from the proximal end 32 of the boom member 28 and internally through the vertical post 36 and the rail clamp 16. The load bearing cable 38 is configured to attach to selectively applied weights 14 in order to place the drive shaft 30 under tension and achieve the desired traction on the arm 26 of the patient 12. The cable/traction system is self-adjusting in length as adjustments are made in regard to positioning of the arm 26. It is also contemplated by this disclosure that the cable/traction system could be housed externally to the boom member 28 and/or vertical post 36.

Figure 2A:
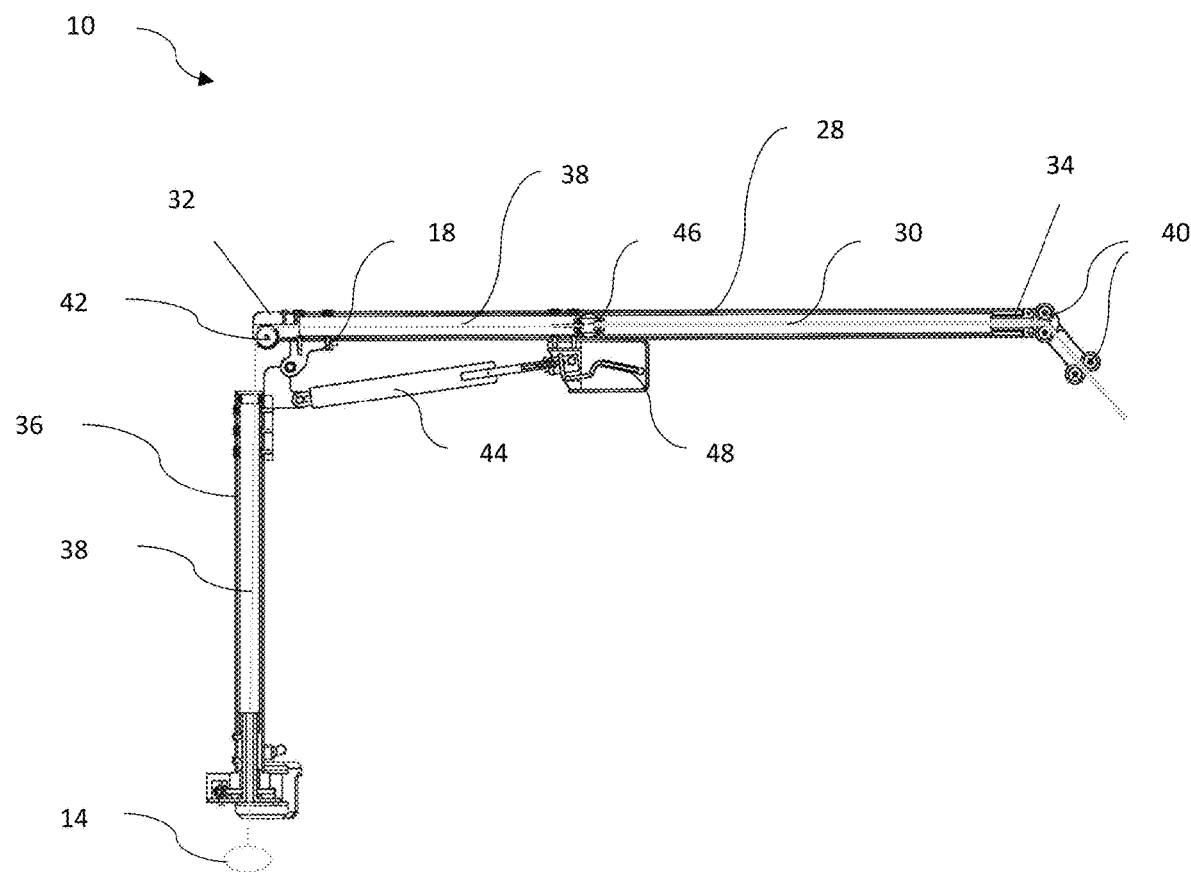
FIG. 2A is a cross-sectional view of the limb positioning apparatus of FIG. 1.
Figure 2B:
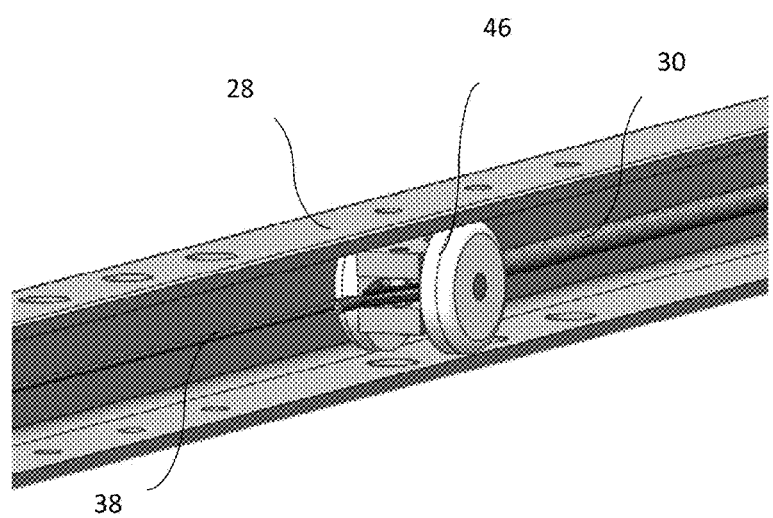
FIG. 2B is a detailed, cross-sectional view of the boom member of the limb positioning apparatus of FIG. 1.

Turning now to FIG. 2A, a cross-sectional view of the limb positioning apparatus 10 is shown. The boom member 28 and the vertical post 36 may be in the form of a generally square tube, as shown in more detail in FIG. 2B. The boom member 28 and vertical post 36 may be made of stainless steel or other suitable materials for maintaining an easily cleaned exterior surface. A carriage 46 is disposed within the boom member 36 and configured for axial movement therein. In examples, the carriage 46 is a wheeled carriage. The load bearing cable 38 is attached a first side of the carriage 46 and extends toward the proximal end 32 of the boom member 36. The load bearing cable 38 is thinner than the drive shaft 30 and is free to rotate. The load hearing cable 38 has a small bend radius to accommodate the tight transition from the boom member 28 to the vertical post 36. At the proximal end 32 of the boom member 28, the load bearing cable 38 exits through an aperture (not shown) and is routed over a single pulley 42. A hook, thimble or other suitable member is attached to the free end of the load bearing cable 38 to which the counter-weights 14 can be added. The drive shaft 30 is attached to the opposite side of the carriage 46 and extends toward the distal end 34 of the boom member 28. The drive shaft 30 is rigidly mounted to the carriage 46 such that it cannot rotate about its longitudinal axis. The drive shaft 30 is configured to transfer the traction load to the operative limb of the patient and bends to accommodate different flexion/extension and abduction adduction angles but resists internal/external rotation. The drive shaft 30 is threaded over a plurality of pulleys 40 at the distal end 34 of the boom member 36. The plurality of pulleys 40 provide an additional anti-rotational resistance to the drive shaft 30. The proximal end 32 of the boom member 28 is attached to a hinge assembly 18 which is coupled to a lockable gas spring 44. The hinge assembly 18 is configured to allow the boom member 28 to move up and down relative to the support member 36 for positioning the arm 26 of the patient 12. The gas spring 44 is coupled to both the vertical post 36 and the boom member 28. The gas spring 44 allows the angle between the vertical post 36 and the boom member 28 to be adjusted by actuation of a lever 48 attached to the end of the gas spring 44, as further described below.

Figure 3A:
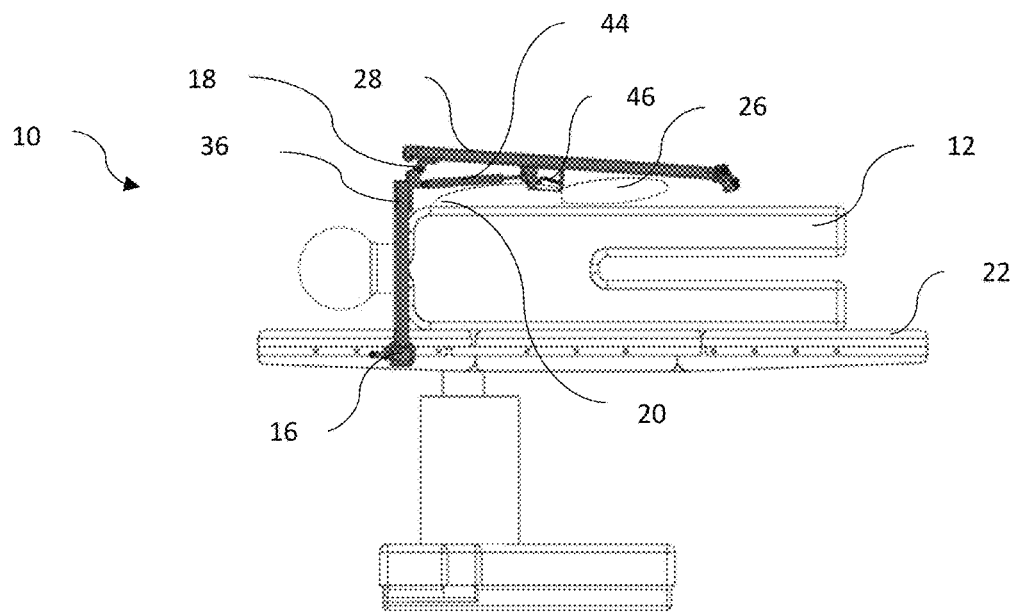
FIGS. 3A and 3B illustrate the use of the limb positioning apparatus of FIG. 1.
Figure 3B:
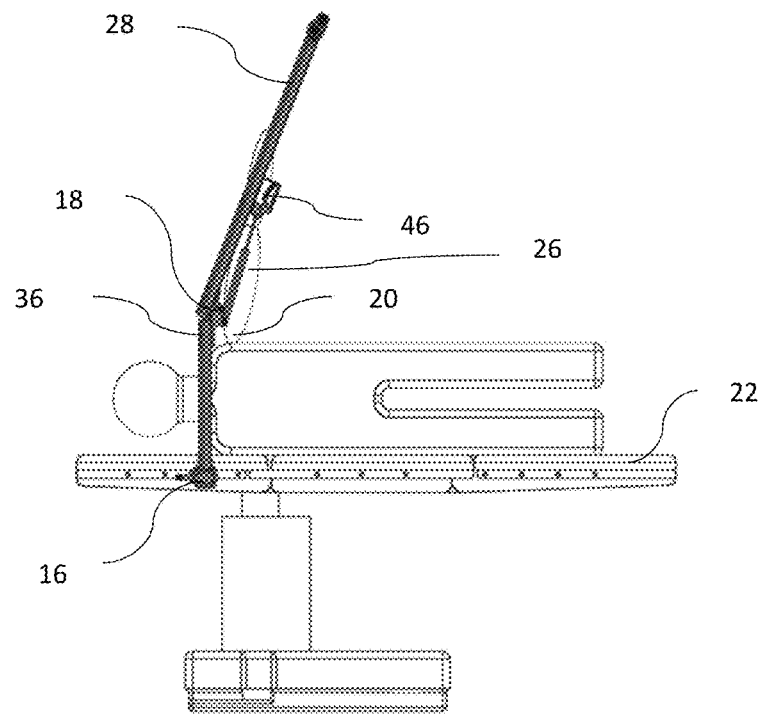

As shown in FIGS. 3A and 3B, the arm 26 of the patient 12 is attached to the apparatus 10 such that the boom member 28 extends along the arm 26 of the patient 12. When the lever 46 of the gas spring 44 is compressed, the angle between the vertical post 36 and the boom member 28 can be adjusted. When the lever 46 is released, the angle between the vertical post 36 and the boom member 28 will become fixed again. Additionally, the gas spring 44 provides lift assistance to the boom member 28 to reduce user fatigue caused by lifting and lowering the boom member 28 with the additional load of the traction weights 14. It is also contemplated by this disclosure that, instead of a gas spring 44, other locking joints (such as pins, gears or friction) could be used.

It will be appreciated that, by placing the centers of the rotation of the shoulder 20 and the hinge assembly 18 close together, the apparatus 10 replicates and follows the natural range of motion of the arm 26 based upon the shoulder 20. This increases the range of motion of the apparatus and, hence, the positions in which the arm 26 can be held. Additionally, by replicating and following the natural range of motion of the arm, the size of the apparatus 10 can be reduced when compared to current systems. By reducing the size of the apparatus 10, the forces and loads on the rail clamp 16 are reduced, specifically when compared to devices that attach to the foot end of the operating table 22. The reduced load means that the apparatus 10 of this disclosure will have less deflection and provide more stable positioning of the arm 26. Furthermore, by reducing the size of the apparatus 10, all controls for the apparatus 10 can be placed within reach of the surgeon, which is more ergonomic and less dependent on the height of the surgeon.

Figure 4A:
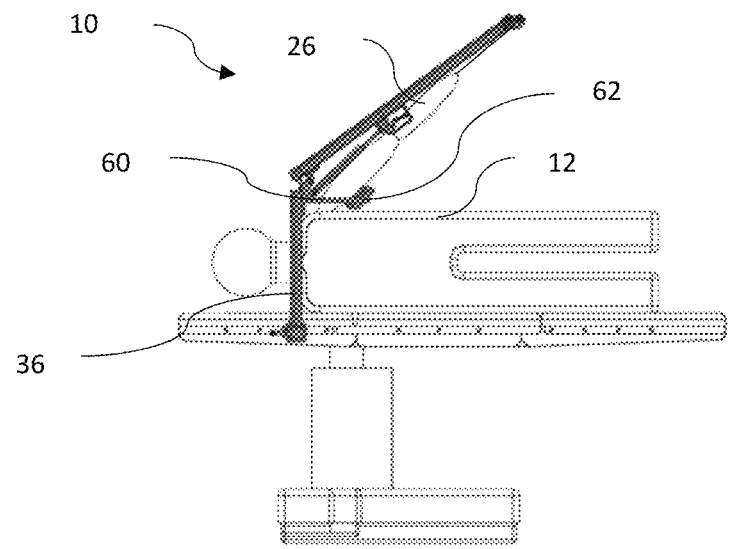
FIGS. 4A and 4B show an alternative example of the limb positioning apparatus of this disclosure with an additional arm support.
Figure 4B:
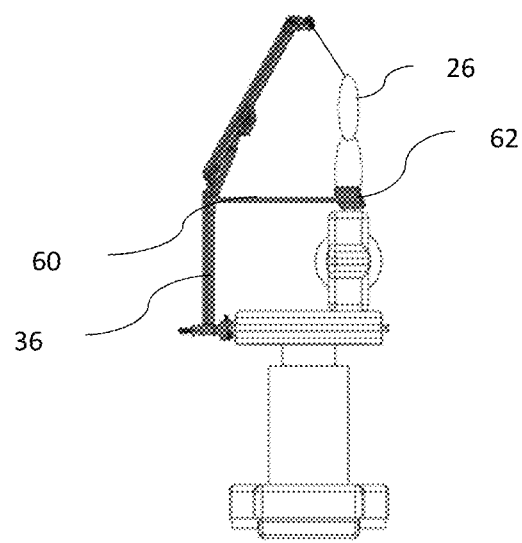

FIGS. 4A and 4B illustrate an additional example of the apparatus 10 of this disclosure which include an additional lift bar 60. The lift bar 60 is designed to accommodate surgical procedures where the arm 26 requires additional lift, such as shoulder instability repairs or elbow procedures. The lift bar 60 is attached to the vertical post 36 and extends towards the patient from the vertical post 36. The lift bar 60 can be rotated and locked in all three directions by means of a multi-directional bracket (not shown). The lift bar 60 can be made from a set of telescoping tubes to allow its length to be adjusted. In examples, the distal end of the lift bar 60 includes a padded member 62, such as a foam pad, for comfortably supporting the arm 26. The padded member 62 and lift bar 60 may be covered in a drape (not shown) to allow adjustment in the sterile field. Advantageously, the lift bar 60 extends below the arm 26 of the patient 12, keeping the lift bar 60 out of the way of the surgeon. Additionally, lift bar 60 is close to the vertical post 36, which reduces the forces and loads on the apparatus 10. The reduced load means that the apparatus 10 will have less deflection and provide a more stable positioning of the arm 26.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A limb positioning apparatus comprising:
   a support member having a proximal end and a distal end, the proximal end configured to be attached to a table adjacent a shoulder of an arm of a patient;
   a boom member extending above and moveable relative to the support member via a hinge assembly coupled between the distal end of the support member and a proximal end of the boom member, the boom member configured to extend along the arm of the patient;
   a cable/traction system extending through the support member and the boom member, a distal end of the cable system configured to be attached to the arm of the patient and a proximal end of the cable system configured to be attached to a weight for providing traction to the arm of the patient; and
   a gas spring operatively connected between the support member and the boom member, the gas spring configured to assist with the movement of the boom member relative to the support member.

2. The apparatus of claim 1, wherein the cable/traction system comprises:
   a carriage disposed within the boom member and moveable along the boom member;
   a first flexible member attached to a first side of the carriage, a free end of the first flexible member configured for attachment to the weight; and
   a second flexible member attached to a second side of the carriage, the second flexible member configured for attachment to the arm of the patient.

3. The apparatus of claim 2, wherein the carriage is a wheeled carriage.

4. The apparatus of claim 3, wherein the support member is rotatable relative to the clamp.

5. The apparatus of claim 2, wherein the first flexible member is attached to the first side of the carriage such that first flexible member can rotate relative to a longitudinal axis of the boom member.

6. The apparatus of claim 2, wherein the second flexible member is attached to the second side of the carriage such that second flexible member cannot rotate relative to a longitudinal axis of the boom member.

7. The apparatus of claim 2, wherein the second flexible member is routed through a plurality of pulleys such that the plurality of pulleys provides an anti-rotational resistance to the second flexible member.

8. The apparatus of claim 2, wherein a diameter of the second flexible member is selected to be larger than a diameter of the first flexible member.

9. The apparatus of claim 2, wherein the proximal end of the support member is configured to be attached to the table by a clamp such that the first flexible member extends through the clamp.

10. The apparatus of claim 1, further comprising a lift bar extending from the support member for supporting an underside of the arm of the patient.

11. The apparatus of claim 10, wherein a distal end of the lift bar comprises a padded member.

12. The apparatus of claim 1, wherein at least one of the support member and the boom member is a square tube.

13. The apparatus of claim 1, wherein the gas spring comprises a lever for locking and unlocking the gas spring.

14. A method of positioning a limb during surgery, comprising:
  attaching an arm of a patient to a limb positioning apparatus, the limb positioning apparatus comprising:
    a support member having a proximal end and a distal end, the proximal end configured to be attached to a table adjacent a shoulder of the arm of the patient;
    a boom member extending above and moveable relative to the support member via a hinge assembly coupled between the distal end of the support member and a proximal end of the boom member, the boom member configured to extend along the arm of the patient;
    a cable/traction system extending through the support member and the boom member, a distal end of the cable system configured to be attached to the arm of the patient and a proximal end of the cable system configured to be attached to a weight for providing traction to the arm of the patient; and
    a gas spring operatively connected between the support member and the boom member; and
  moving the boom member relative to the support member such that the operative limb of the patient is placed in a pre-selected position.

15. The method of claim 14, further comprising attaching the limb positioning apparatus to the table adjacent the shoulder of the patient with a clamp such that the proximal end of the cable system extends through the clamp.

16. The method of claim 15, further comprising rotating the support member relative to the clamp.

17. The method of claim 14, further comprising actuating a lever of the gas spring such that the boom member is moveable relative to the support member.

18. The method of claim 14, further comprising locking the boom member relative to the support member by actuating a lever of the gas spring.

19. The method of claim 14, wherein the cable/traction system is self-adjusting in length as the boom member is moved relative to the support member.

20. The method of claim 14, further comprising supporting the arm of the patient with a lift bar extending from the support member toward the patient.

* * * * *